United States Patent [19]  [11] 4,336,255
Ladd  [45] Jun. 22, 1982

[54] PHARMACEUTICAL COMPOSITIONS CONTAINING GUANIDINOPYRIMIDINES
[75] Inventor: David L. Ladd, Overbrook Hills, Pa.
[73] Assignee: SmithKline Corporation, Philadelphia, Pa.
[21] Appl. No.: 247,049
[22] Filed: Mar. 24, 1981
[51] Int. Cl.³ .............. A61K 31/505; C07D 239/30; C07D 239/48
[52] U.S. Cl. .................. 424/251; 544/326
[58] Field of Search ............ 544/326; 424/251
[56] References Cited
U.S. PATENT DOCUMENTS 2,295,563  9/1942  D'Alelio et al. ............ 544/326
2,422,887  6/1947  Curd et al. ............... 544/325
2,487,569  11/1949 Mackey .................. 544/323
3,284,188  11/1966 Amagasa et al. ........... 544/323

OTHER PUBLICATIONS

Buehler et al., "Chem. Ber.", vol. 99, pp. 2997–3007.
Carbon, "J. Org. Chem.", vol. 26, 1961, pp. 455–461.

Primary Examiner—Donald G. Daus
Assistant Examiner—James H. Turnipseed
Attorney, Agent, or Firm—William H. Edgerton; Richard D. Foggio; Alan D. Lourie

[57] ABSTRACT

Pharmaceutical compositions having as active diuretic ingredients certain 4-guanidinopyridines are described. Representative diuretic compounds are 5-amino-6-chloro-4-guanidinopyrimidine and 6-amino-5-nitro-4-guanidinopyrimidine.

12 Claims, No Drawings

PHARMACEUTICAL COMPOSITIONS CONTAINING GUANIDINOPYRIMIDINES

This invention comprises new pharmaceutical compositions whose active ingredients are chemical compounds whose basic structures have a pyrimidine ring with a guanidino substituent at the 4-position and either an amino or nitro group at the 5-position. The dosage unit compositions of this invention have diuretic activity and, more precisely, natiuretic activity. Also part of this invention is a series of new 5-amino-4-guanidinopyrimidines.

DESCRIPTION OF THE PRIOR ART

Few amino-4-guanidinopyrimidines are known to the art; E. Buehler et al., Chem. Ber. 99 2997 (1966). This publication describes a 2-dimethylamino-4-guanidinopyrimidine. 6-Amino-5-nitro-4-guanidinopyrimidine is described as a chemical intermediate in J. A. Carbon, J. Org. Chem. 26 455 (1961). None of these publications suggest the substitution pattern of the structures of the 5-amino-4-guanidinopyrimidines of this invention or the biological activity of these and of the corresponding 5-nitro-4-guanidinopyrimidines.

DESCRIPTION OF THE INVENTION

The new compounds of this invention are represented by the following structural formula:

$$\begin{array}{c}\text{R}\\ \text{N}\underset{3}{\overset{6}{\underset{2}{\bigcirc}}}\text{5}\text{—NH}_2\\ \text{N}\text{—NH—C—NH}_2\\ \|\\ \text{NH}\end{array} \quad \text{I}$$

in which:

R is halo, that is fluoro, chloro, bromo or iodo, or amino.

A subgeneric group of compounds of this invention are those of structure I in which either R is chloro or amino.

Pharmaceutical dosage units and methods of inducing diuretic activity in patients in need thereof are also part of this invention and are described hereafter using as an active ingredient a compound of the formula:

$$\begin{array}{c}\text{R}\\ \text{N}\bigcirc\text{—R}_1\\ \text{N}\text{—NH—C—NH}_2\\ \|\\ \text{NH}\end{array} \quad \text{II}$$

in which R is as described above and $R_1$ is amino or nitro.

Also included in this invention are the pharmaceutically acceptable acid addition salts of the bases of the structural formulas I and II above formed by reaction with nontoxic inorganic or organic acids such as hydrochloric, hydrobromic, hydriodic, sulfuric, phosphoric, sulfamic, ethane disulfonic, methane sulfonic, acetic, maleic or nitric acids. The salts are prepared conveniently by mixing a lower alkanol solution of the base with an excess of the acid such as with reacting the base in methanol with hydrogen chloride in ethyl ether.

The chemical compounds related to this invention are prepared either by replacement of the reactive 4-halo substituent on a 5-amino or nitro-4-halopyrimidine by guanidine or, in case of the 5-amino series, by catalytic hydrogenation of a 5-nitro-4-guanidinopyrimidine. In the former reaction, guanidine in at least one molar equivalent, is reacted with the desired 4-halopyrimidine in a suitable organic solvent such as methanol or ethanol usually at reflux temperature until the reaction is complete. In the second reaction a suitable hydrogenation catalyst known to be effective for hydrogenating nitro groups in an organic solvent may be used. Such catalysts are Raney nickel or a noble metal catalyst such as platinum oxide or palladium. Raney nickel in 2-methoxyethanol is often used.

The compounds of this invention of the formula II have diuretic activity which can be demonstrated in standard pharmacological tests. More specifically these compounds have natriuretic activity in the sodium deficient rat test. Generally natriuretic activity was demonstrated in this test at 30 mg/kg with these new compounds. Standard diuretic compounds such as hydrochlorothiazide or triamterene show activity at 5 or 15 mg/kg respectively.

Following is the protocol of the sodium deficient rat test and representative results using compounds of this invention as active ingredients.

Normal male rats weighing 175–203 g are placed on a sodium deficient diet for a period of 5 days. On the morning of the 5th day food is removed for the duration of the experiment. On day 6, water is also removed and the rats are loaded with 3.0 ml of 0.85% sodium chloride (s.c.) and 5 ml of water (p.o.). There are 8 animals in the control group and in each test group. The test compound is given orally. Urine samples are collected 6 hours after dosing.

| Compound | Dose mg/kg Salt | Base | No. of Rats | Electrolytes excreted uEg/rat Na⊕/K⊕ | | Na⊕/K⊕ ratio |
|---|---|---|---|---|---|---|
| 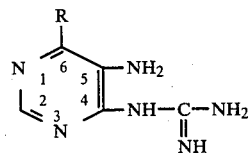 0.9HCl | 17.6 | 15.0 | 8 | 11 | 176 | 0.063 |
| | 35.3 | 30.0 | 8 | 48* | 248* | 0.192 |
| Control | — | — | 8 | 2 | 63 | 0.037 |
| NH₂ pyrimidine-NHCNH₂·H₂SO₄ | 23.8 | 15.0 | 8 | 13* | 77 | 0.178 |
| | 47.6 | 30.0 | 8 | 16* | 88 | 0.181 |
| Control | — | — | 8 | 4 | 64 | 0.077 |
| 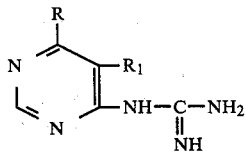 | 5.0 | 8 | 3 | 55 | 0.051 |
| | 10.0 | 8 | 91* | 107 | 0.813* |
| | 15.0 | 8 | 73* | 99 | 0.730* |
| | 30.0 | 8 | 78* | 92 | 0.836* |
| Control | — | — | 8 | 2 | 69 | 0.028 |

In the same pharmacological procedure a well known diuretic compound, hydrochlorothiazide gave the following results:

| | 5 | — | | 31.6 | 355.9 | .087 |
|---|---|---|---|---|---|---|
| | 30 | — | | 82.6 | 198.6 | 0.411 |

The potassium sparing diuretic, triamterene, gave the following results:

| | 15 | — | | 64.9 | 53.4 | 1.213 |
|---|---|---|---|---|---|---|
| | 30 | — | | 154.4 | 56.1 | 2.730 |

*statistically significant

Oral doses of the compounds selected from the range of about 10–50 mg/kg (indicating weight of base/body weight) have a natriuretic activity, most pronounced without limiting side effects at a dose selected from the range of 15–30 mg/kg, depending on the activity of the active ingredient as noted.

The 5-nitro-4-guanidinopyrimidine series also demonstrates a potassium sparing effect together with enhanced naturetic activity.

The pharmaceutical compositions of this invention containing a compound of Formula II which has diuretic activity are prepared in conventional dosage unit forms by combining the chemical compound, or a pharmaceutically acceptable acid addition salt thereof, with a nontoxic pharmaceutical carrier according to accepted procedures in a nontoxic amount sufficient to produce the desired pharmacodynamic activity in a subject, animal or human. The compositions will contain the active ingredient in an active but nontoxic quantity selected from about 75 mg to about 500 mg of active base ingredient per dosage unit but this quantity depends on the specific biological activity desired, the activity of the compound and the condition of the patient.

A wide variety of pharmaceutical forms can be employed. Thus, if a solid carrier for oral administration is used the preparation can be tableted, placed in a hard gelatin capsule in powder or pellet form, or in the form of a suppository, trouche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing diuretic activity comprises administering internally to a subject in need of such activity a compound of Formula II or a pharmaceutically acceptable acid addition salt thereof, usually combined with a pharmaceutical carrier, in a nontoxic amount sufficient to produce said activity as described above. The route of administration may be any route which effectively transports the active compound to the site of action which is to be affected within the kidney such as orally or parenterally. Advantageously, equal oral doses will be administered several times such as 2–5 times a day with the daily dosage regimen being selected from about 150 mg to about 1.5 g.

The following examples are designed solely to illustrate the preparation and use of the compounds of this invention. The temperatures are Centigrade. The doses outlined herein are in terms of the base form of the compounds of the Formula II. Other variations of these examples will be obvious to those skilled in the art.

EXAMPLE 1

A mixture of 5.70 g (0.0289 mole) of 6-amino-4-guanidino-5-nitropyrimidine and 500 ml of 2-methoxyethanol was hydrogenated over Raney nickel at 60° for 20 min. at 3.10 KPS. The warm mixture was filtered and concentrated; the brown residue was slurried in a warm mixture of 2-methoxyethanol and water then made acidic with 10% sulfuric acid. The cooled mixture was filtered. The solid was washed with water and ethanol to give 6.2 g (81%) of 5,6-diamino-4-guanidinopyrimidine sulfate. A purified sample was prepared by hot trituration of the crude product with 50% aqueous 2-methoxyethanol followed by methanol wash to give a product with mp 305° (dec.).

Anal. Calc'd. for $C_5H_9N_7.H_2SO_4$: C, 22.64; H, 4.18; N, 36.96. Found: C, 23.04; H, 4.11; N, 37.33.

EXAMPLE 2

A mixture of 6.87 g (0.0419 mole) of 4,6-dichloro-5-aminopyrimidine and absolute ethanol containing a large excess of guanidine free base was heated at reflux overnight. The solution was cooled to room temperature, filtered and the filtrate concentrated to an orange oil which was triturated with water giving a solid which was separated by filtration and dried to 0.74 g (9.5%) of 5-amino-6-chloro-4-guanidinopyrimidine. The hydrochloride salt was prepared in methanol-ether, mp 230°.

Anal. Calc'd. for $C_5H_7ClN_6.0.9$ HCl: C, 27.37; H, 3.63; N, 38.30. Found: C, 27.35; H, 3.69; N, 38.61.

Repeating this reaction with 4,6-dibromo-5-aminopyrimidine prepared as is the dichloroaminopyrimidine gives 5-amino-6-bromo-4-guanidinopyrimidine hydrobromide. Other 6-halo congeners are made by variations of these reactions.

EXAMPLE 3

6-Amino-4-guanidino-5-nitropyrimidine and its hydrochloride salt to be used as an active ingredient are prepared by the method described by J. A. Carbon, J. Org. Chem. 26 459 (1961). Other 5-nitropyrimidines are prepared by the reactions described in that publication and in the above examples such as the following:

A mixture of 10 g of 4,6-dichloro-5-nitropyrimidine in ethanol is reacted at reflux for three days with a slight excess of guanidine to give 4-guanidino-6-chloro-5-nitropyrimidine.

EXAMPLE 4

| Ingredient | Mg. per Tablet |
| --- | --- |
| 6-Amino-4-guanidino-5-nitropyrimidine | 150 |
| Corn starch | 15 |
| Polyvinylpyrrolidone | 12 |
| Magnesium stearate | 3 |
| Corn starch | 16 |

The first two ingredients are mixed and wet granulated. The granules are dried, mixed with the remaining ingredients and compressed into scored tablets which are administered to a patient in need of diuretic activity from 2–5 times daily.

What is claimed is:

1. A method of inducing diuretic activity in a patient in need thereof comprising administering orally or by injection a nontoxic diuretic quantity of a compound of the basic formula:

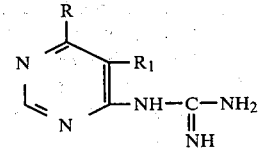

in which:

R is halo or amino; and $R_1$ is amino or nitro; together with the pharmaceutically acceptable, acid addition salts thereof.

2. The method of claim 1 in which the compound is 4-guanidino-6-amino-5-nitropyrimidine or a pharmaceutically acceptable acid addition salt thereof.

3. The method of claim 1 in which the compound is 4-guanidino-6-chloro-5-aminopyrimidine or a pharmaceutically acceptable acid addition salt thereof.

4. The method of claim 1 in which the compound is 4-guanidino-5,6-diaminopyrimidine or a pharmaceutically acceptable acid addition salt thereof.

5. The method of claims 1, 2, 3 or 4 in which an oral dosage unit containing a quantity of active ingredient selected from the range of 75–500 mg is administered from 2–5 times daily.

6. A pharmaceutical composition in dosage unit form having diuretic activity comprising a nontoxic diuretic quantity of a compound of the basic formula:

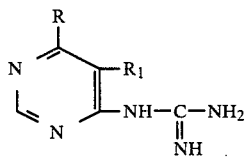

in which:

R is halo or amino; and $R_1$ is amino or nitro; together with the pharmaceutically acceptable, acid addition salts thereof and a carrier therefor.

7. The composition of claim 6 in which the compound is 4-guanidino-6-amino-5-nitropyrimidine or a pharmaceutically acceptable salt thereof.

8. The composition of claim 6 in which the compound is 4-guanidino-6-chloro-5-aminopyrimidine or a pharmaceutically acceptable salt thereof.

9. The composition of claims 6, 7 or 8 in which the quantity of compound is selected from the range of 75–500 mg adapted for oral administration.

10. A compound of the basic formula:

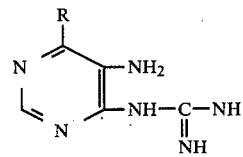

in which R is halo or amino; together with the pharmaceutically acceptable, acid addition salts thereof.

11. The compound of claim 10 being 4-guanidino-6-chloro-5-aminopyrimidine or one of its pharmaceutically acceptable, acid addition salts.

12. The compound of claim 10 being 4-guanidino-5,6-diaminopyrimidine or one of its pharmaceutically acceptable acid addition salts.

* * * * *